(12) United States Patent
Yang et al.

(10) Patent No.: US 10,387,713 B2
(45) Date of Patent: Aug. 20, 2019

(54) APPARATUS AND METHOD OF PROCESSING MEDICAL IMAGE

(71) Applicant: SAMSUNG MEDISON CO., LTD., Hongcheon-gun (KR)

(72) Inventors: Sun-mo Yang, Hongcheon-gun (KR); Gil-ju Jin, Hongcheon-gun (KR); Yu-ri Kim, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 15/796,188

(22) Filed: Oct. 27, 2017

(65) Prior Publication Data

US 2018/0046846 A1     Feb. 15, 2018

Related U.S. Application Data

(63) Continuation of application No. 14/994,256, filed on Jan. 13, 2016, now Pat. No. 9,818,019.

(30) Foreign Application Priority Data

Jul. 7, 2015  (KR) ........................ 10-2015-0096779

(51) Int. Cl.
| | |
|---|---|
| *G06K 9/00* | (2006.01) |
| *A61B 8/00* | (2006.01) |
| *G06F 3/01* | (2006.01) |
| *G06F 21/32* | (2013.01) |
| *G06F 3/041* | (2006.01) |

(52) U.S. Cl.
CPC ............ *G06K 9/00087* (2013.01); *A61B 8/00* (2013.01); *A61B 8/467* (2013.01); *A61B 8/54* (2013.01); *G06F 3/011* (2013.01); *G06F 21/32* (2013.01); *G06F 3/041* (2013.01)

(58) Field of Classification Search
CPC ........ G06K 9/0087; A61B 8/00; A61B 8/467; A61B 8/54; G06F 3/011; G06F 21/32; G06F 3/041
See application file for complete search history.

(56) References Cited

U.S. PATENT DOCUMENTS

| | | | |
|---|---|---|---|
| 6,129,671 A | 10/2000 | Hastings | |
| 6,773,398 B2 | 8/2004 | Ogasawara et al. | |
| 8,443,199 B2 | 5/2013 | Kim et al. | |
| 8,717,141 B2 | 5/2014 | Eberhart et al. | |
| 9,489,127 B2* | 11/2016 | Kim | ....................... G06F 3/041 |
| 9,652,061 B2* | 5/2017 | North | ...................... G06F 3/041 |

(Continued)

FOREIGN PATENT DOCUMENTS

| | | | |
|---|---|---|---|
| EP | 2865338 A1 | 4/2015 | |
| EP | 2913769 A1 | 9/2015 | |

(Continued)

OTHER PUBLICATIONS

Communication dated Nov. 15, 2016, issued by the European Patent Office in counterpart European application No. 16153326.0.

*Primary Examiner* — Gregory M Desire
(74) *Attorney, Agent, or Firm* — Sughrue Mion, PLLC

(57) ABSTRACT

An apparatus for processing medical images includes a storage unit storing fingerprints that respectively correspond to a plurality of functions, a user input unit detecting a fingerprint of a user, and a controller performing a function corresponding to the detected fingerprint, from among the functions.

14 Claims, 15 Drawing Sheets

(56) References Cited

U.S. PATENT DOCUMENTS

| | | |
|---|---|---|
| 9,818,019 B2 * | 11/2017 | Yang .................. G06K 9/00087 |
| 2005/0041841 A1 | 2/2005 | Yoo et al. |
| 2005/0054926 A1 | 3/2005 | Lincoln |
| 2005/0080326 A1 | 4/2005 | Mathew |
| 2008/0097205 A1 | 4/2008 | Takimoto et al. |
| 2012/0212455 A1 | 8/2012 | Kloeffel |
| 2013/0141366 A1 * | 6/2013 | Ritter ...................... G06F 3/041 345/173 |
| 2014/0369572 A1 | 12/2014 | Setlak |
| 2015/0033231 A1 | 1/2015 | Wu |
| 2015/0036065 A1 | 2/2015 | Yousefpor et al. |
| 2015/0199553 A1 | 7/2015 | Kim et al. |
| 2015/0220259 A1 | 8/2015 | Ban et al. |
| 2015/0220767 A1 | 8/2015 | Yoon et al. |
| 2015/0277652 A1 | 10/2015 | Kim |
| 2015/0381617 A1 | 12/2015 | Jung et al. |
| 2017/0177820 A1 * | 6/2017 | Zhang ................. G06F 19/3418 |
| 2018/0046846 A1 * | 2/2018 | Yang ....................... G06F 21/32 |

FOREIGN PATENT DOCUMENTS

| | | |
|---|---|---|
| JP | 2006-141506 A | 6/2006 |
| JP | 2006-526437 A | 11/2006 |
| KR | 10-2010-0104648 A | 9/2010 |
| KR | 10-2014-0024858 A | 3/2014 |
| KR | 10-2014-0128071 A | 11/2014 |

* cited by examiner

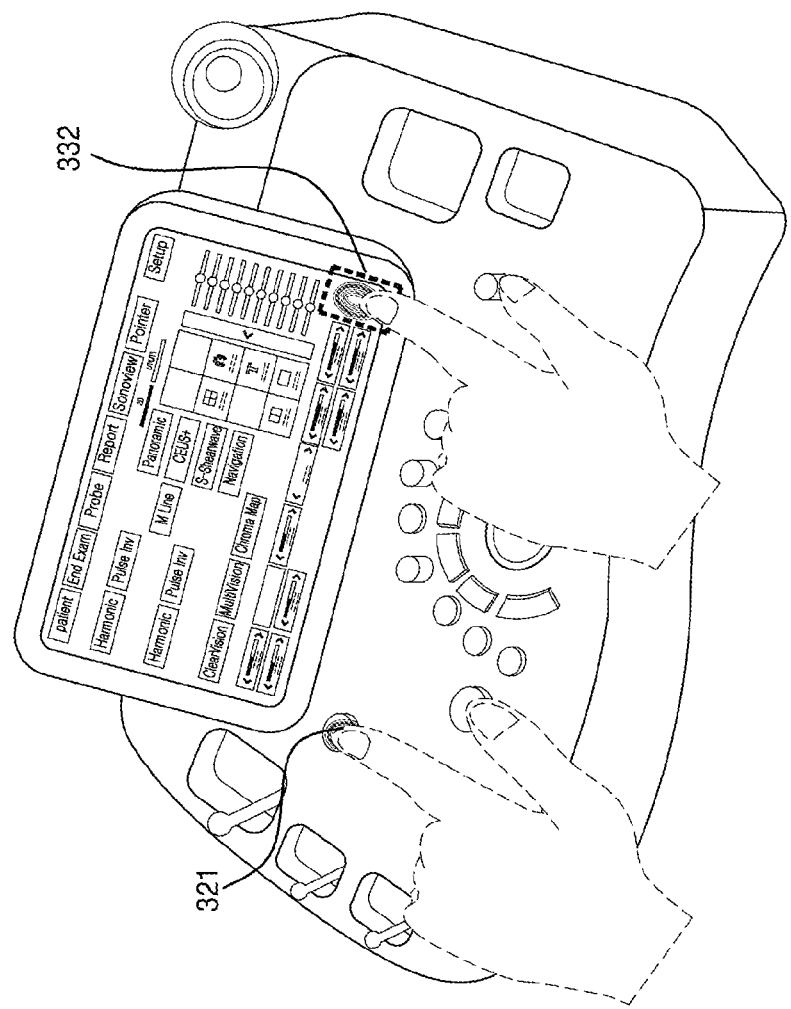
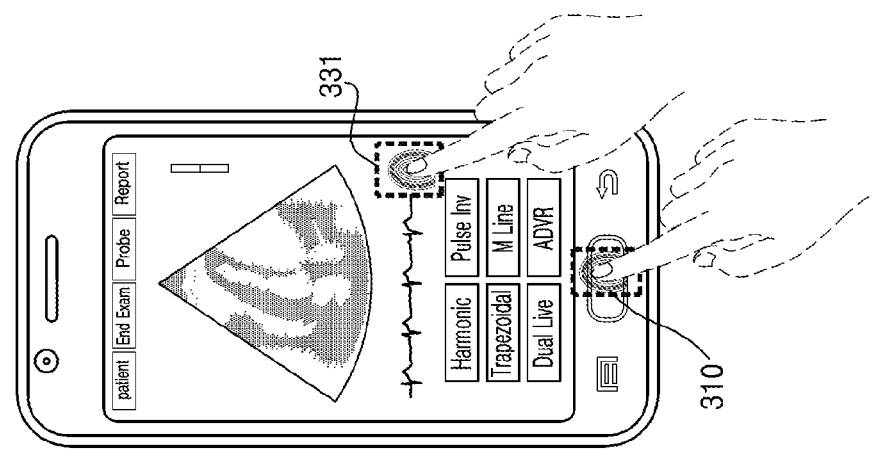
FIG. 3B
FIG. 3A

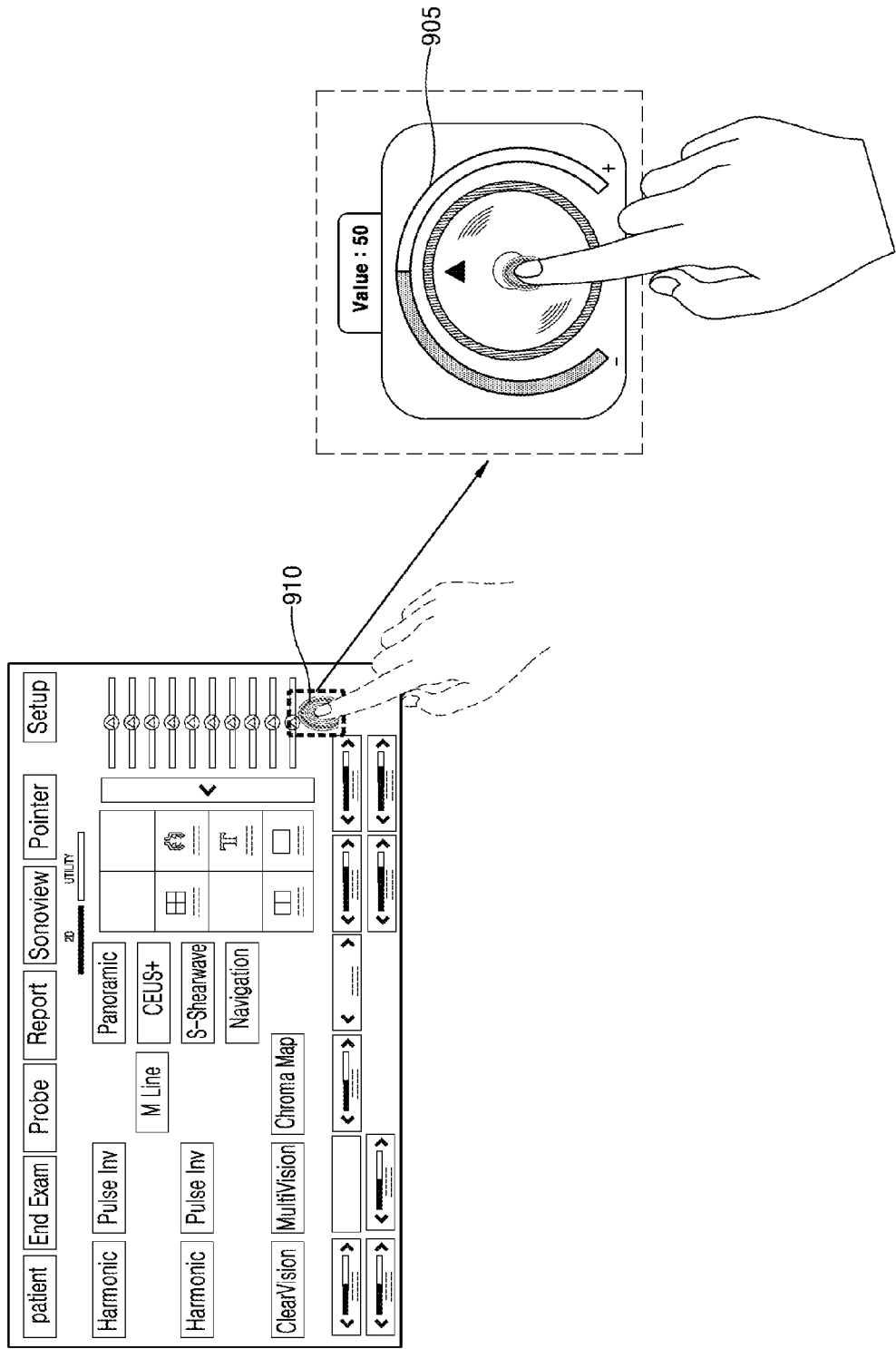

APPARATUS AND METHOD OF PROCESSING MEDICAL IMAGE

CROSS-REFERENCE TO RELATED APPLICATION

This application is a continuation of U.S. patent application Ser. No. 14/994,256, filed on Jan. 13, 2016, which claims the benefit of Korean Patent Application No. 10-2015-0096779, filed on Jul. 7, 2015, in the Korean Intellectual Property Office, the disclosures of which are incorporated herein by reference in their entireties.

BACKGROUND

1. Field

The present disclosure relates to an apparatus and method of processing medical images, and more particularly, to an apparatus and method of processing medical images, in which various functions are performed using fingerprints of a user.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

The ultrasound diagnosis apparatuses may provide a brightness (B) mode in which reflection parameters of ultrasound signals that are reflected from an object are shown as 2-dimensional (2D) images, a Doppler mode in which an image of a moving object (in particular, blood flow) is shown by using the Doppler effect, and an elastic mode in which a difference between applying and not applying compression onto an object is shown via an image.

SUMMARY

Provided are an apparatus for processing medical images which stores fingerprints corresponding to various functions, and when a fingerprint of a user is detected, performing a function corresponding to the detected fingerprint, and a method of operating the apparatus.

Additional aspects will be set forth in part in the description which follows and, in part, will be apparent from the description, or may be learned by practice of the presented exemplary embodiments.

According to an aspect of an exemplary embodiment, an apparatus for processing medical images includes a storage configured to store fingerprints that respectively correspond to a plurality of functions, a user input unit configured to detect a fingerprint of a user, and a controller configured to perform a function corresponding to the detected fingerprint, from among the functions.

In an embodiment, the apparatus further includes a display configured to display guide information that is related to the function corresponding to the detected fingerprint.

In an embodiment, the user input unit includes a touch screen, and the touch screen displays, at a point where the fingerprint of the user is detected, guide information related to the function corresponding to the detected fingerprint.

In an embodiment, the functions include at least one of a freeze function, a time gain compensation (TGC) adjustment function, and a Doppler related function.

In an embodiment, the user input unit includes at least one of a key button, a knob button, a trackball, and a dial touchpad.

In an embodiment, when a first fingerprint of the user is detected, the controller performs a first function corresponding to the first fingerprint from among the functions, and when a second fingerprint of the user is detected, the controller performs a second function corresponding to the second fingerprint from among the functions.

In an embodiment, when the first and second fingerprints are detected, the controller performs a third function from among the functions.

In an embodiment, when the function corresponding to the detected fingerprint is a function of adjusting a value, the controller adjusts the value according to a rotation direction and a rotation angle of the detected fingerprint.

In an embodiment, when the detected fingerprint is a first fingerprint, the controller increases or decreases the value by a first value when the first fingerprint rotates by a predetermined angle, and when the detected fingerprint is a second fingerprint, the controller increases or decreases the value by a second value when the second fingerprint rotates by a predetermined angle.

In an embodiment, the user input unit detects a user input for rotating the detected fingerprint, and the controller performs a function that is different from the function corresponding to the detected fingerprint according to a rotation direction and a rotation angle of the detected fingerprint.

According to an aspect of another exemplary embodiment, a method of operating an apparatus for processing medical images includes storing fingerprints that respectively correspond to a plurality of functions, detecting a fingerprint of a user, and performing a function corresponding to the detected fingerprint, from among the functions.

In an embodiment, the method further includes displaying guide information that is related to the function corresponding to the detected fingerprint.

In an embodiment, the displaying of the guide information includes displaying, at a point where the fingerprint of the user is detected, guide information related to the function corresponding to the detected fingerprint.

In an embodiment, the performing of the function corresponding to the detected fingerprint includes, when a first fingerprint of the user is detected, performing a first function corresponding to the first fingerprint from among the functions, and when a second fingerprint of the user is detected, performing a second function corresponding to the second fingerprint from among the functions.

In an embodiment, the performing of the function corresponding to the detected fingerprint further includes, when the first and second fingerprints are detected, performing a third function from among the functions.

In an embodiment, the performing of the function corresponding to the detected fingerprint includes, when the function corresponding to the detected fingerprint is a function of adjusting a value, adjusting the value according to a rotation direction and a rotation angle of the detected fingerprint.

In an embodiment, the adjusting of the value includes, when the detected fingerprint is a first fingerprint, increasing or decreasing the value by a first value when the first fingerprint rotates by a predetermined angle, and when the detected fingerprint is a second fingerprint, increasing or decreasing the value by a second value when the second fingerprint rotates by a predetermined angle.

In an embodiment, the method further includes detecting a user input for rotating the detected fingerprint, and performing a function that is different from the function corresponding to the detected fingerprint according to a rotation direction and a rotation angle of the detected fingerprint.

BRIEF DESCRIPTION OF THE DRAWINGS

Embodiments of the invention now will be described more fully hereinafter with reference to the accompanying drawings, in which reference numerals denote structural elements.

FIGS. 3A and 3B are diagrams of a user input unit of FIG. 1;

FIGS. 9A and 9B are diagrams for describing a method of adjusting values by using a fingerprint of a user, according to an exemplary embodiment;

DETAILED DESCRIPTION

Figure 1:
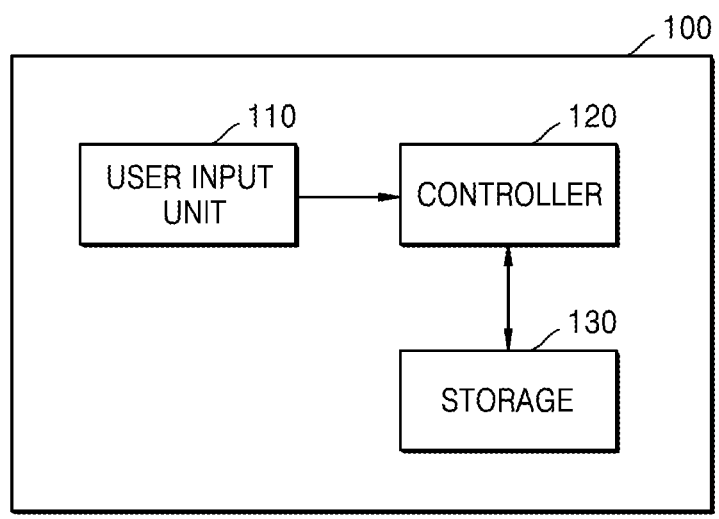
FIG. 1 is a block diagram of an apparatus for processing medical images, according to an exemplary embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "image" may refer to multi-dimensional data including discrete image components. For example, an image may include, but is not limited to, a medical image (an ultrasound image, a computed tomography (CT) image, or a magnetic resonance (MR) image) of an object obtained by an ultrasound apparatus, a CT apparatus, or an MRI apparatus.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

An ultrasound image may refer to an image obtained by transmitting ultrasound signals generated by a transducer of a probe to an object and receiving echo signals reflected from the object. The ultrasound image may be at least one of, for example, an amplitude (A) mode image, a brightness (B) mode image, a color (C) mode image, and a Doppler (D) mode image. Also, according to an exemplary embodiment, the ultrasound image may be a 2-dimensional (2D) image or a 3-dimensional (3D) image.

The CT image may refer to a synthesized image of a plurality of X-ray images that are obtained by capturing an object while rotating about at least one axis of the object.

The MR image may refer to an image of an object obtained based on the MRI principle.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

FIG. 1 is a block diagram of an apparatus 100 for processing medical images, according to an exemplary embodiment. Referring to FIG. 1, the apparatus 100 may include a user input unit 110, a controller 120, and a storage 130.

The storage 130 according to an exemplary embodiment may store fingerprints that respectively correspond to a plurality of functions performed to process the medical images. The functions may include, but is not limited to, a Doppler image photography function (a color Doppler image photography function or a power Doppler image photography function), a pulse wave measurement function, a freeze function, a time gain compensation (TGC) adjustment function, a focus selection function, a parameter measurement function, a storage function, an S-Detect function, and an E-Breast function.

The storage 130 may respectively match the functions to fingerprints of a user and store the fingerprints. For example, a fingerprint corresponding to a first function among the functions may be set as a thumb fingerprint of a first user, a fingerprint that corresponding to a second function may be set as an index finger fingerprint of the first user, and a fingerprint corresponding to a third function may be set as a middle finger fingerprint of the first user. Alternatively, a fingerprint corresponding to a fourth function may be set as a thumb fingerprint of a second user, and a fingerprint corresponding to a fifth function may be set as an index finger fingerprint of the second user. However, exemplary embodiments are not limited thereto.

The user input unit 110 may include a fingerprint sensor to detect the fingerprint of the user. Also, the user input unit 110 may detect a user input for rotating the detected fingerprint.

The user input unit 110 may include, for example, a touch screen, a touch panel, a key button, a knob button, a trackball, a dial, and a slide bar.

The touch screen and the touch panel are input devices via which the user may input information by touching. The key button generates manipulation signals by pressing a button. The knob button generates manipulation signals corresponding to a direction depending on which of up, down, left, and right keys of the knob button is pressed. The trackball generates manipulation signals according to a rotation of the ball. The dial generates manipulation signals according to a rotation of the dial. The slide bar generates manipulation signals as a protruding part is moved along a track.

The controller 120 may control overall operations of the apparatus 100. The controller 120 according to the exemplary embodiment may perform a function that corresponds to a fingerprint detected by the user input unit 110. For example, when the user input unit 110 detects a first fingerprint, the controller 120 may perform a first function that corresponds to the first fingerprint, and when the user input unit 110 detects a second fingerprint, the controller 120 may perform a second function that corresponds to the second fingerprint. Alternatively, when the first fingerprint and the second fingerprint are detected at the same time by the user input unit 110, the controller 120 may perform a third function.

Also, when a function corresponding to a detected fingerprint is a function of adjusting a value, the controller 120 may adjust the value according to a rotation direction and a rotation angle of the detected fingerprint. For example, when the detected fingerprint is a first fingerprint, the controller 120 may increase or decrease the value by a first value when the first fingerprint rotates by a predetermined angle. Alternatively, when the detected fingerprint is a second fingerprint, the controller 120 may increase or decrease the value by a second value when the second fingerprint rotates by a predetermined angle.

Also, the controller 120 may perform a function that is different from a function corresponding to a detected fingerprint according to a rotation direction and a rotation direction of the detected fingerprint.

Figure 2:
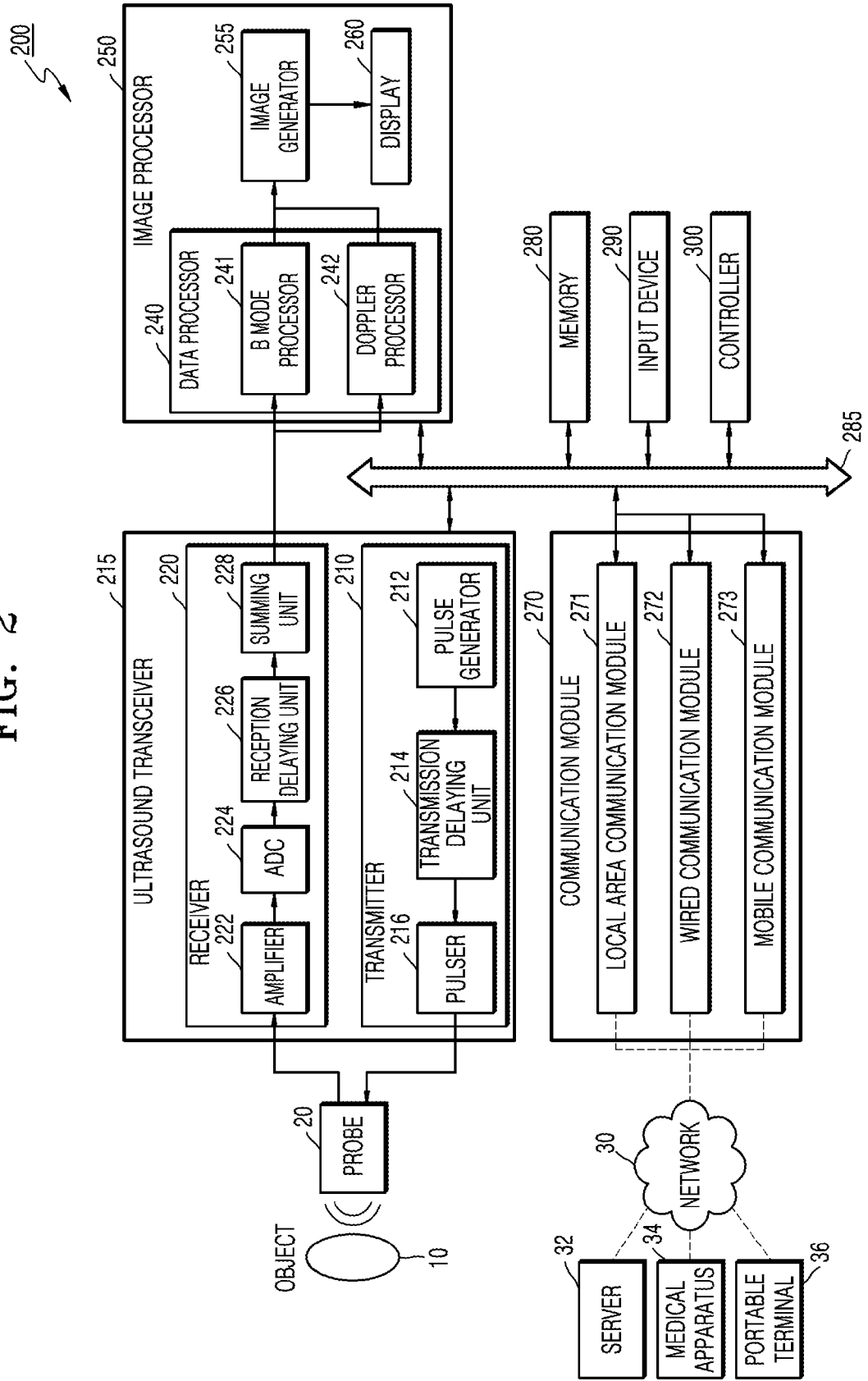
FIG. 2 is a block diagram of an apparatus for processing medical images, according to an exemplary embodiment.

FIG. 2 is a block diagram of an apparatus 200 for processing medical images, according to an exemplary embodiment.

Referring to FIG. 2, the apparatus 200 according to the exemplary embodiment may be an ultrasound diagnosis apparatus. The ultrasound diagnosis apparatus 200 may include a probe 20, an ultrasound transceiver 215, an image processor 250, a communication module 270, a display 260, a memory 280, an input device 290, and a controller 295, which may be connected to one another via buses 285.

The storage 130 of FIG. 1 may correspond to the memory 280 of FIG. 2, the user input unit 110 of FIG. 1 may correspond to the input device 290 of FIG. 2, and the controller 120 of FIG. 1 may correspond to the controller 295 of FIG. 2. The features of the components (110, 120, and 130) described with reference to FIG. 1 may also be applied to respective components (280, 290, and 295) of FIG. 2. Therefore, the identical features will not be repeatedly described herein.

In some embodiments, the ultrasound diagnosis apparatus 200 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 215 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 200 by wire or wirelessly, and according to embodiments, the ultrasound diagnosis apparatus 200 may include a plurality of probes 20.

A transmitter 210 supplies a driving signal to the probe 20. The transmitter 110 includes a pulse generator 212, a transmission delaying unit 214, and a pulser 216. The pulse generator 212 generates pulses for forming transmission ultrasound waves based on a predetermined pulse repetition frequency (PRF), and the transmission delaying unit 214 delays the pulses by delay times necessary for determining transmission directionality. The pulses which have been delayed correspond to a plurality of piezoelectric vibrators included in the probe 20, respectively. The pulser 216 applies a driving signal (or a driving pulse) to the probe 20 based on timing corresponding to each of the pulses which have been delayed.

A receiver 220 generates ultrasound data by processing echo signals received from the probe 20. The receiver 120 may include an amplifier 222, an analog-to-digital converter (ADC) 224, a reception delaying unit 226, and a summing unit 228. The amplifier 222 amplifies echo signals in each channel, and the ADC 224 performs analog-to-digital conversion with respect to the amplified echo signals. The reception delaying unit 226 delays digital echo signals output by the ADC 1124 by delay times necessary for determining reception directionality, and the summing unit 228 generates ultrasound data by summing the echo signals processed by the reception delaying unit 1126. In some embodiments, the receiver 220 may not include the amplifier 222. In other words, if the sensitivity of the probe 20 or the capability of the ADC 224 to process bits is enhanced, the amplifier 222 may be omitted.

The image processor 250 generates an ultrasound image by scan-converting ultrasound data generated by the ultrasound transceiver 215 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color flow image), a tissue Doppler image showing a movement of tissue, or a spectral Doppler image showing a moving speed of an object as a waveform.

A B mode processor 241 extracts B mode components from ultrasound data and processes the B mode components. An image generator 255 may generate an ultrasound image indicating signal intensities as brightness based on the extracted B mode components 241.

Similarly, a Doppler processor 242 may extract Doppler components from ultrasound data, and the image generator 255 may generate a Doppler image indicating a movement of an object as colors or waveforms based on the extracted Doppler components.

According to an embodiment, the image generator 255 may generate a three-dimensional (3D) ultrasound image via volume-rendering with respect to volume data and may also generate an elasticity image by imaging deformation of the object 10 due to pressure.

Furthermore, the image generator 255 may display various pieces of additional information in an ultrasound image by using text and graphics. In addition, the generated ultrasound image may be stored in the memory 280.

The display 260 displays the generated ultrasound image. The display 260 may display not only an ultrasound image, but also various pieces of information processed by the ultrasound diagnosis apparatus 200 on a screen image via a graphical user interface (GUI). In addition, the ultrasound diagnosis apparatus 200 may include two or more displays 260 according to embodiments.

The display 260 may include at least one of a liquid crystal display, a thin film transistor-liquid crystal display, an organic light-emitting diode display, a flexible display, a 3D display, and an electrophoretic display.

When the display 260 and a user input unit form a layer structure and configured as a touch screen, the display 260 may be not only used as an output device, but also as an input device for the user to input information by touch.

The touch screen may be configured to detect not only a touch input location, and a touched area, but also pressure of the touch. Also, the touch screen may be configured to detect not only real-touch but also proximity touch.

The display 260 according to the exemplary embodiment may display guide information related to a function corresponding to a fingerprint detected by the input device 290. Also, when the display 260 is configured as a touch screen, the guide information related to the function may be displayed at a point where the fingerprint is detected.

The communication module 270 is connected to a network 30 by wire or wirelessly to communicate with an external device or a server. The communication module 270 may exchange data with a hospital server or another medical apparatus in a hospital, which is connected thereto via a PACS. Furthermore, the communication module 170 may perform data communication according to the digital imaging and communications in medicine (DICOM) standard.

The communication module 270 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 270 may receive information about a diagnosis history or medical treatment schedule of a patient from a server and utilizes the received information to diagnose the patient. Furthermore, the communication module 270 may perform data communication not only with a server or a medical apparatus in a hospital, but also with a portable terminal of a medical doctor or patient.

The communication module 270 is connected to the network 30 by wire or wirelessly to exchange data with a server 32, a medical apparatus 34, or a portable terminal 36. The communication module 270 may include one or more components for communication with external devices. For example, the communication module 270 may include a local area communication module 271, a wired communication module 272, and a mobile communication module 273.

The local area communication module 271 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 272 refers to a module for communication using electric signals or optical signals. Examples of wired communication techniques according to an embodiment may include communication via a twisted pair cable, a coaxial cable, an optical fiber cable, and an Ethernet cable.

The mobile communication module 273 transmits or receives wireless signals to or from at least one selected from a base station, an external terminal, and a server on a mobile communication network. The wireless signals may be voice call signals, video call signals, or various types of data for transmission and reception of text/multimedia messages.

The memory 280 stores various data processed by the ultrasound diagnosis apparatus 200. For example, the memory 180 may store medical data related to diagnosis of an object, such as ultrasound data and an ultrasound image that are input or output, and may also store algorithms or programs which are to be executed in the ultrasound diagnosis apparatus 200.

The memory 280 may be any of various storage media, e.g., a flash memory, a hard disk drive, EEPROM, etc. Furthermore, the ultrasound diagnosis apparatus 100 may utilize web storage or a cloud server that performs the storage function of the memory 280 online.

The memory 280 according to the exemplary embodiment may store fingerprints of the user that respectively correspond to functions in the ultrasound diagnosis apparatus 200. A first fingerprint of a first user and a second fingerprint of a second user may be matched with an identical function and stored. Alternatively, the first fingerprint (e.g., a thumb fingerprint of the first user) and a third fingerprint (e.g., a middle finger fingerprint of the first user) of the first user may be matched with an identical function and stored.

The input device 290 refers to a means via which a user inputs data for controlling the ultrasound diagnosis apparatus 50. The input device 290 may include hardware components, such as a keypad, a mouse, a touch pad, a touch screen, and a jog switch. Also, the input device 290 may include a fingerprint sensor and detect the fingerprints of the user. The input device 290 may further include any of various other input units including an electrocardiogram (ECG) measuring module, a respiration measuring module, a voice recognition sensor, a gesture recognition sensor, an iris recognition sensor, a depth sensor, a distance sensor, etc. In particular, the input device 290 may include a touch screen in which the touch pad and the display 260 form a mutual layer structure.

The ultrasound diagnosis apparatus 200 according to an exemplary embodiment may display an ultrasound image of a predetermined mode and a control panel related to the ultrasound image on the touch screen. Also, the ultrasound diagnosis apparatus 200 may detect a touch gesture of the user related to the ultrasound image via the touch screen.

From among buttons included in a control panel of a typical ultrasound apparatus, the ultrasound diagnosis apparatus 200 according to an exemplary embodiment may physically include some buttons that are frequently used by the user and provide other buttons in a graphical user interface (GUI) form via the touch screen.

The controller 295 may control all operations of the ultrasound diagnosis apparatus 200. In other words, the controller 295 may control operations among the probe 20, the ultrasound transceiver 200, the image processor 250, the communication module 270, the memory 280, and the input device 290 shown in FIG. 1.

All or some of the probe 20, the ultrasound transceiver 215, the image processor 250, the display 260, the communication module 270, the memory 280, the input device 290, and the controller 295 may be implemented as software modules. However, embodiments of the present invention are not limited thereto, and some of the components stated above may be implemented as hardware modules. Also, at least one of the ultrasound transmission/reception unit 215, the image processor 250, and the communication module 270 may be included in the control unit 295; however, the inventive concept is not limited thereto.

FIGS. 3A and 3B are diagrams of the user input unit 110 of FIG. 1.

Referring to FIGS. 3A and 3B, the user input unit 110 may include a key button, a knob button, a trackball, a dial, etc. For example, when the user touches a key button 310 by using a finger, the key button 310 may detect a fingerprint of the user by using a fingerprint sensor. Alternatively, as shown in FIG. 3B, when the user touches a key button 321 by using a finger, the touched key button 321 may detect a fingerprint of the user by using a fingerprint sensor. The user input unit 110 may include a fingerprint sensor even when including the knob button, the trackball, and the dial.

Also, the user input unit 110 may include a touch screen. For example, as shown in FIGS. 3A and 3B, when the user touches touch screens 331 and 332, the touch screens 331 and 332 may detect the fingerprint of the user by using fingerprint sensors. In this case, the touch screens 331 and 332 may detect the fingerprint of the user in all areas or only in some predetermined areas.

Figure 4:
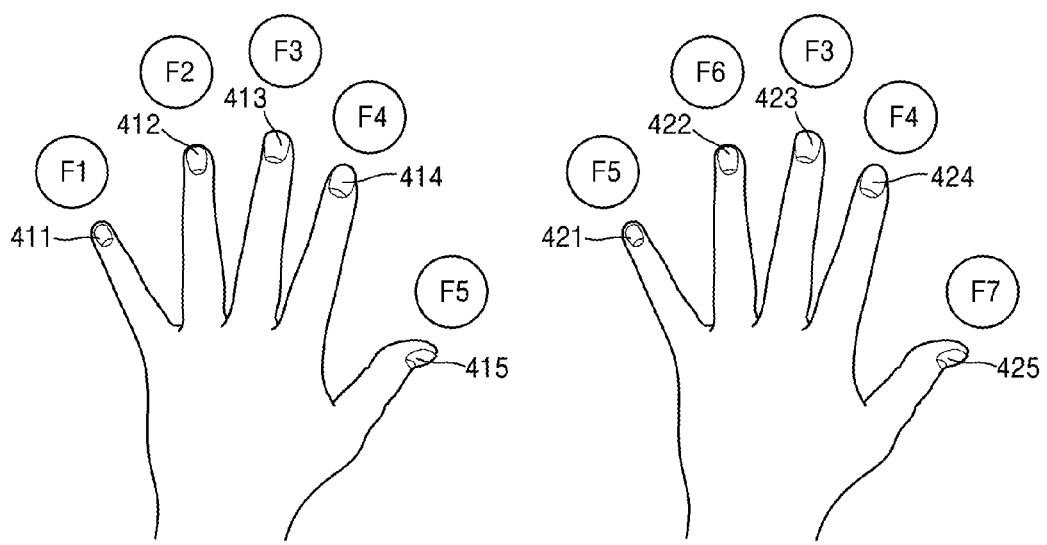
FIG. 4 is a diagram illustrating a method of assigning functions to fingerprints of a user, according to an exemplary embodiment.

FIG. 4 is a diagram illustrating a method of assigning functions to fingerprints of a user, according to an exemplary embodiment.

Referring to FIG. 4, functions may be assigned to each fingerprint of the first user. For example, the apparatus 100 may assign a first function F1 to a baby finger fingerprint 411 of the first user, a second function F2 to a ring finger fingerprint 412, a third function F3 to a middle finger fingerprint 413, a fourth function F4 to an index finger fingerprint 414, and a fifth function F5 to a thumb fingerprint 415. The functions assigned to the fingerprints of the user may be set according to user settings. The set functions may be matched with the fingerprints and stored in the storage 130.

Also, the apparatus 100 may assign functions to each fingerprint of the second user. In this case, the functions may be different from or the same as those assigned to the fingerprints of the first user. For example, the fifth function F5 may be assigned to a baby finger fingerprint 421 of the second user as the thumb fingerprint 415 of the first user, the third function F3 may be assigned to a middle finger fingerprint 423 as the middle finger fingerprint 413 of the first user, and the fourth function F4 may be assigned to an index finger fingerprint 424 as the index finger fingerprint 414 of the first user. Also, a sixth function F6 may be assigned to a ring finger fingerprint 422 of the second user, and a seventh function F7 may be assigned to a thumb fingerprint 425. The apparatus 100 may match the fingerprints with the functions assigned to each of the fingerprints and store the matched fingerprints.

The apparatus 100 may match the fingerprints to an identical function and store the matched fingerprints. For example, as shown in FIG. 4, the fifth function may be matched with the thumb fingerprint 415 of the first user and the baby finger fingerprint 421 of the second user.

Figure 5A:
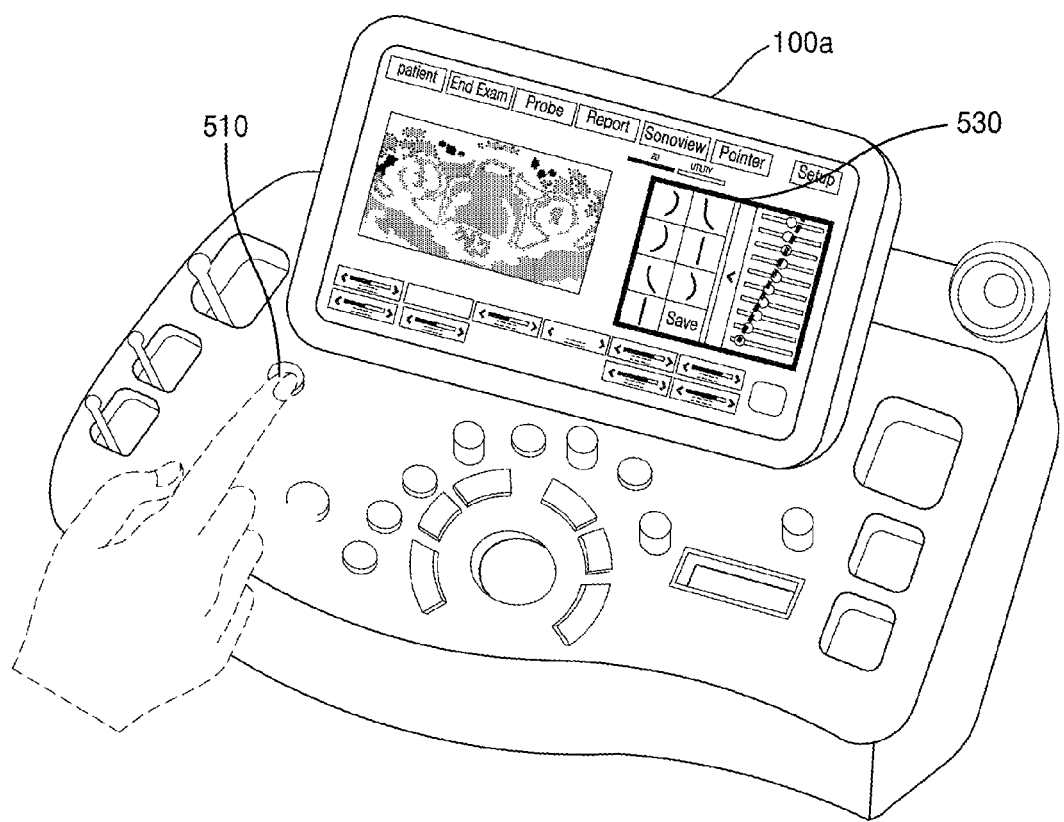
FIGS. 5A to 5C are diagrams for describing a method of operating an apparatus for processing medical images when a fingerprint of a user is detected, according to an exemplary embodiment.
Figure 5B:
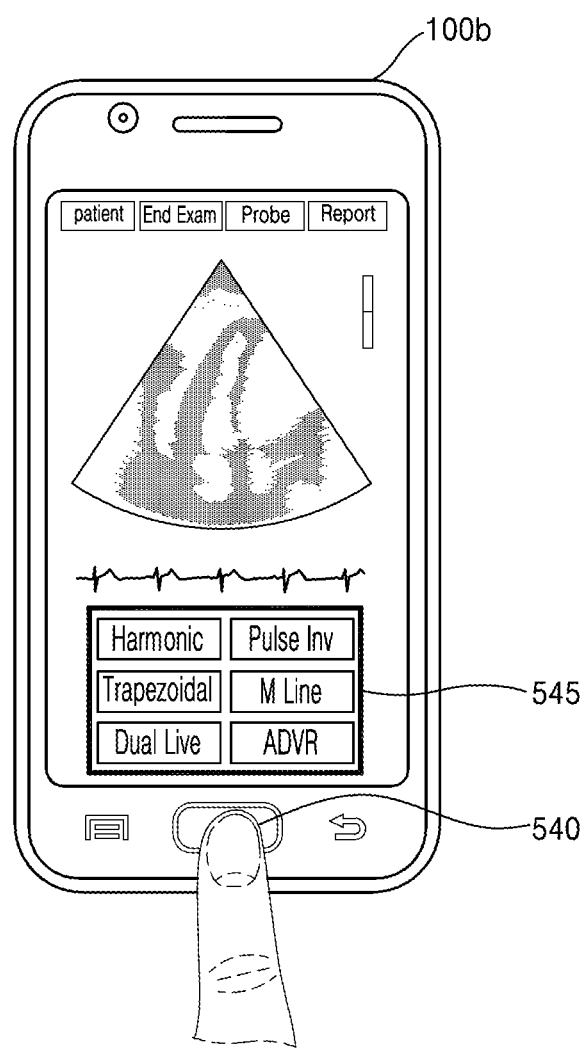
Figure 5C:
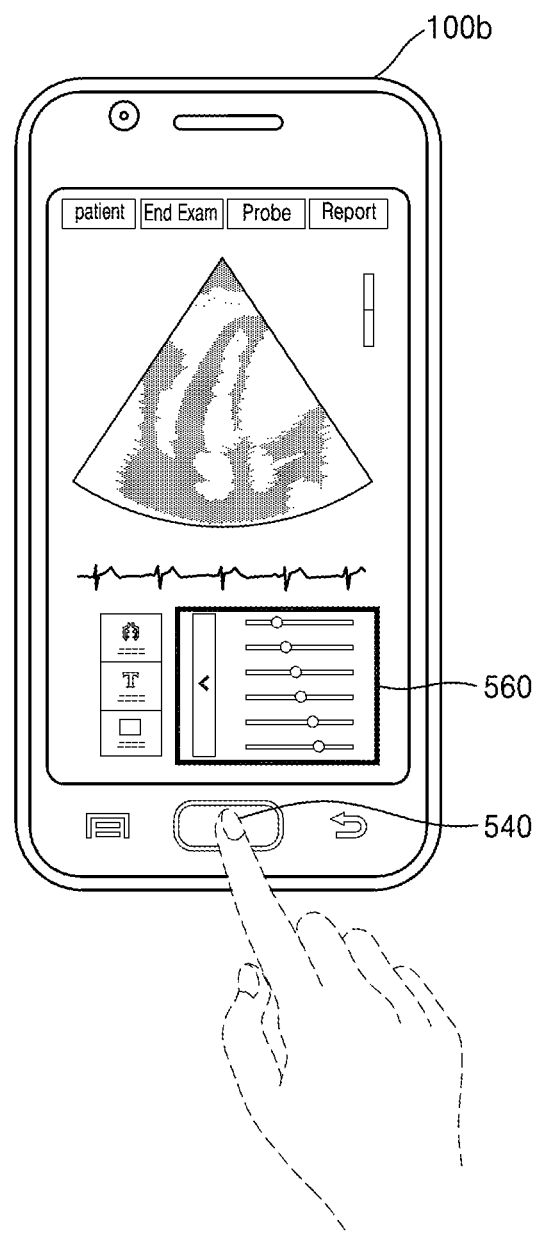

FIGS. 5A to 5C are diagrams for describing a method of operating an apparatus for processing medical images when a fingerprint of a user is detected, according to an exemplary embodiment.

The apparatus 100 according to the exemplary embodiment may include a first apparatus 100*a* for processing medical images and a second apparatus 100*b* for processing medical images.

As shown in FIG. 5A, when the user touches a first key button 510 by using an right hand index finger, the first key button 510 may detect a fingerprint of the right hand index finger of the user by using a fingerprint sensor. The first apparatus 100*a* may display guide information related to a function corresponding to the detected fingerprint on a display. For example, when a function corresponding to the fingerprint of the right hand index finger of the user is set to the TGC adjustment function, the apparatus 100 may display a TGC adjustment menu 530 on the display. The TGC adjustment menu 530 may include, for example, a menu for selecting shapes of TGC curves and a menu for setting a TGC value according to a depth of an image. Also, as shown in FIG. 5B, when the user touches a second key button 540 by using the thumb, the second key button 540 may detect a thumb fingerprint of the user by using a fingerprint sensor. When a function corresponding to the thumb fingerprint of the user is set to a B mode image display function, the second apparatus 100*b* may display a B mode image menu 545 on a display. For example, a B mode image menu 545 may include, but is not limited to, a harmonic function, a pulse inv function, a trapezoidal function, an M line function, a dual live function, an agile digital video recorder (ADVR) function, a Doppler image photography (C-Mode) function, and a power Doppler image photography (PW-Mode) function.

The harmonic function is for configuring a screen by only using harmonic components of frequencies in a B mode image. The pulse inv function is for configuring a screen by scanning two times to completely remove fundamentals other than the harmonic components of frequencies in the B mode image and thereby obtaining a harmonic image. The trapezoidal function is for converting a linear image into a trapezoidal image. The M line function is for setting a line for obtaining an M mode image. The dual live function is for simultaneously displaying a 2D image and a color Doppler image, or simultaneously displaying a 2D image and a power Doppler image. The ADVR function is for real-time storage of a certain area of an image displayed on a display in a DVD format by using a built-in recorder in an apparatus for processing medical images, without an additional external DVD recorder, and reproducing the stored image. The color Doppler image photography function is for capturing a color Doppler image that shows blood flow via color. The power Doppler image photography function is for capturing a power Doppler image that shows velocity of blood flow in waveforms.

Also, as shown in FIG. 5C, when the user touches the second key button 540 by using the right hand index finger, the second key button 540 may detect the fingerprint of the right hand index finger of the user by using the fingerprint sensor. When a function corresponding to the fingerprint of the right hand index finger of the user is set to the TGC adjustment function, the second apparatus 100b may display a TGC adjustment menu 560 on the display. The TGC adjustment menu 560 may include, for example, a menu for setting a TGC value according to a depth of an image.

Function-fingerprint matching information stored in the first apparatus 100a may be also stored in the second apparatus 100b. For example, the first apparatus 100a may set the fingerprint of the right hand index finger of the user to the TGC function and store this information. Then, the first apparatus 100a may transmit function-fingerprint matching information (e.g., TGC function-fingerprint of the right hand index finger) to the second apparatus 100b. The second apparatus 100b may store the function-fingerprint matching information transmitted from the first apparatus 100a. Accordingly, as in the first apparatus 100a, the TGC function may be set to the fingerprint of the right hand index finger of the user in the second apparatus 100b.

Figure 6A:
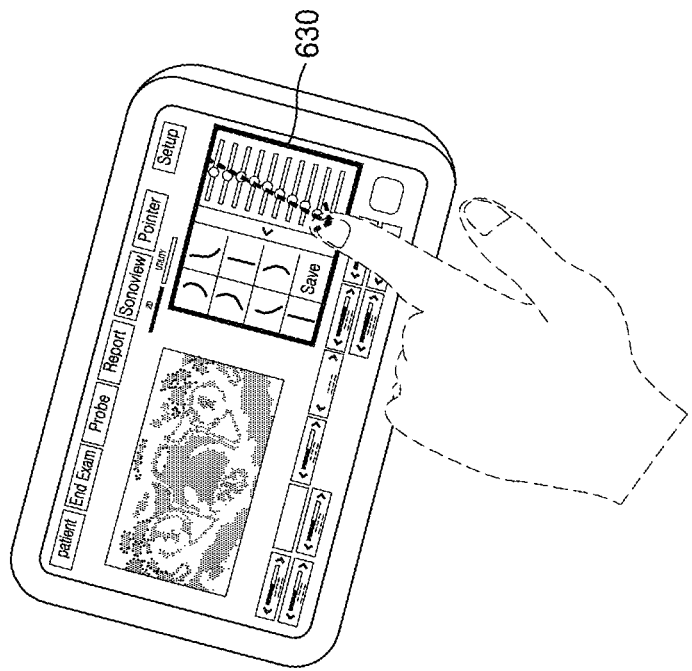
FIGS. 6A and 6B are diagrams for describing a method of operating an apparatus for processing medical images when a fingerprint of a user is detected, according to an exemplary embodiment.
Figure 6B:
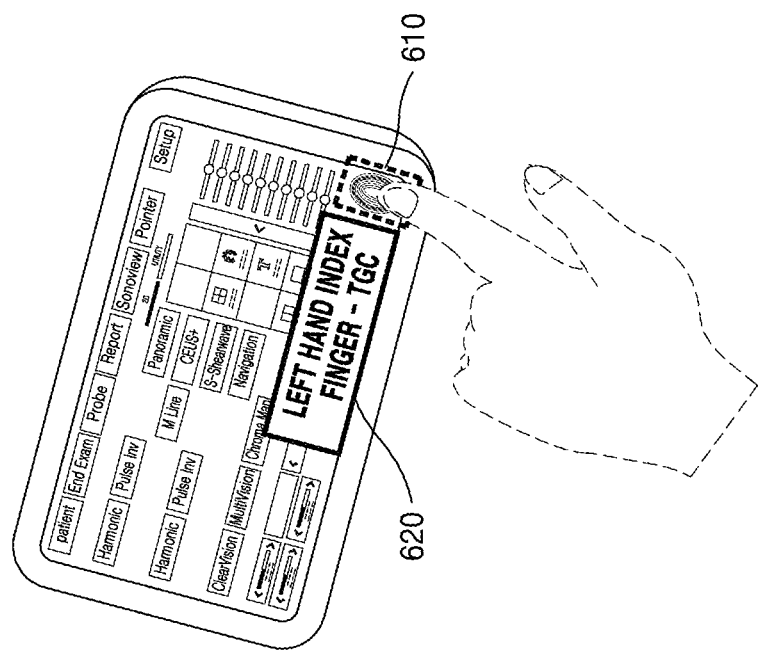

FIGS. 6A and 6B are diagrams for describing a method of operating an apparatus for processing medical images when a fingerprint of a user is detected, according to an exemplary embodiment.

As shown in FIG. 6A, when the user touches a touch screen 610 by using a left hand index finger, the touch screen 610 may detect a fingerprint of the left hand index finger of the user by using a fingerprint sensor.

The apparatus 100 may display guide information 620 that includes information of the detected fingerprint and information of a function corresponding to the detected fingerprint on a touch screen. For example, as shown in FIG. 6A, the apparatus 100 may display the guide information 620 indicating that the left hand left hand index finger fingerprint is detected and the TGC adjustment function is set to the left hand index finger fingerprint. Therefore, the user may easily recognize the function that is set to the fingerprint.

When a fingerprint of the user is detected for a predetermined time or longer, the apparatus 100 may perform a function set to the detected fingerprint. For example, when the guide information 620 is displayed and a fingerprint of the user is detected for a predetermined time, the apparatus 100 may determine that the user has an intent to perform a function corresponding to the detected fingerprint, and thus, as shown in FIG. 6B, may perform the TGC adjustment function and display a TGC adjustment menu 630.

Alternatively, when the fingerprint of the user is not detected for a predetermined time, the apparatus 100 may not perform the function that is set to the detected fingerprint. For example, when guide information is displayed and the user removes the finger that was touching the touch screen, the apparatus 100 may determine that the user does not have an intent to perform a function corresponding to the detected fingerprint, and thus, may not display the guide information nor perform the TGC adjustment function.

Figure 7A:
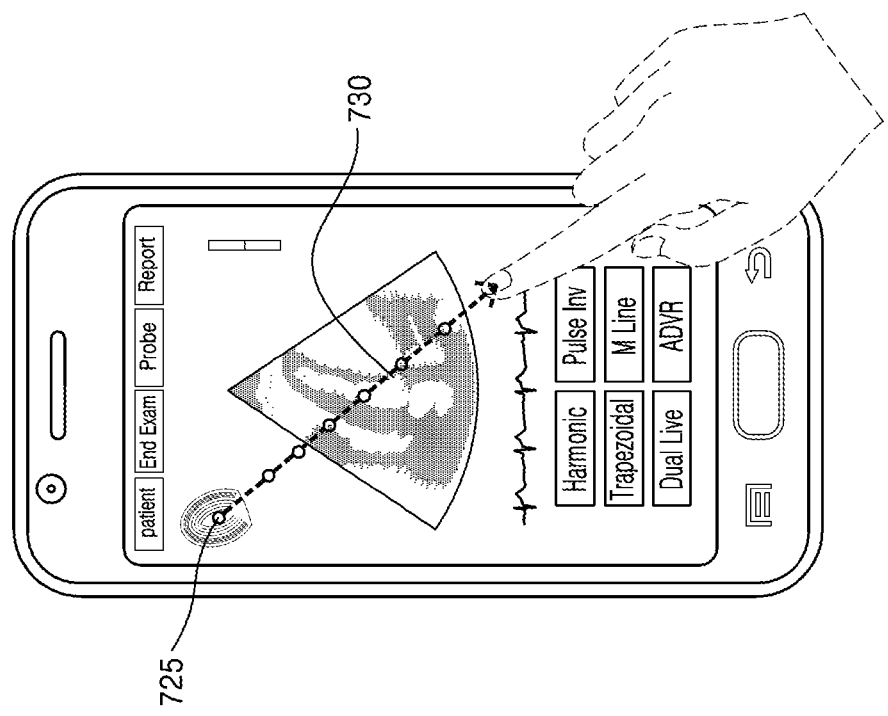
FIGS. 7A and 7B are diagrams for describing a method of operating an apparatus for processing medical images when a fingerprint of a user is detected, according to an exemplary embodiment.
Figure 7B:
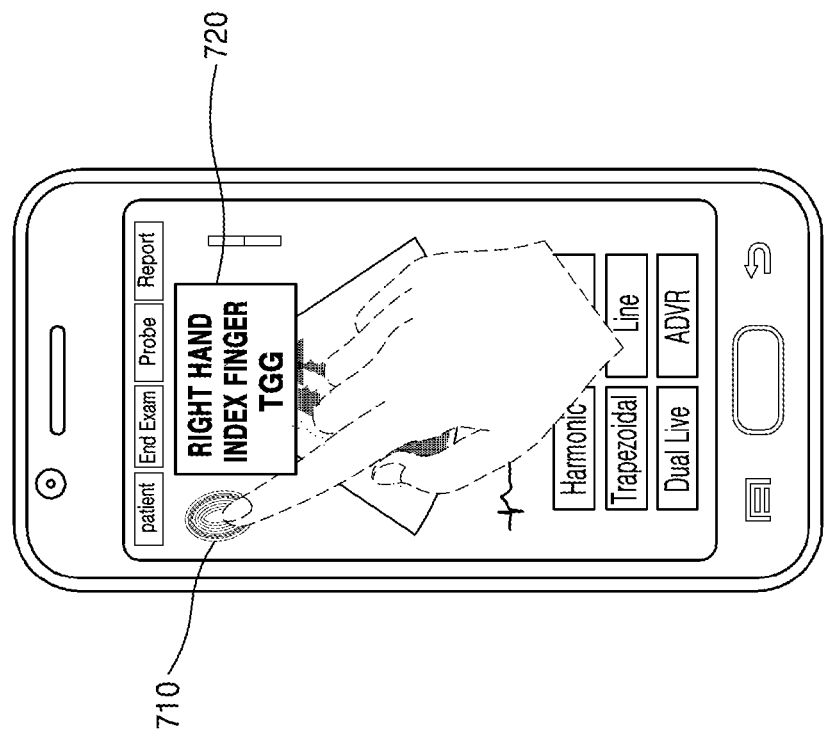

FIGS. 7A and 7B are diagrams for describing a method of operating an apparatus for processing medical images when a fingerprint of a user is detected, according to an exemplary embodiment.

As shown in FIG. 7A, when the user touches a touch screen by using a right hand index finger, the touch screen may detect a fingerprint of the right hand index finger of the user by using a fingerprint sensor.

When a fingerprint 710 of the right hand index finger is detected, the apparatus 100 may display guide information 720 indicating that the fingerprint 710 is detected and the TGC adjustment function is set to the fingerprint 710.

When the fingerprint of the right hand index finger is detected for a predetermined time or longer, the apparatus 100 may perform the TGC adjustment function. For example, as shown in FIG. 7B, when an ultrasound image is displayed on the touch screen, the user may draw a TGC curve 730 by touching and dragging on the ultrasound image based on a point 725 where the fingerprint has been detected. Based on the TGC curve 730, the apparatus 100 may set a TGC value according to a depth of the ultrasound image.

Figure 8:
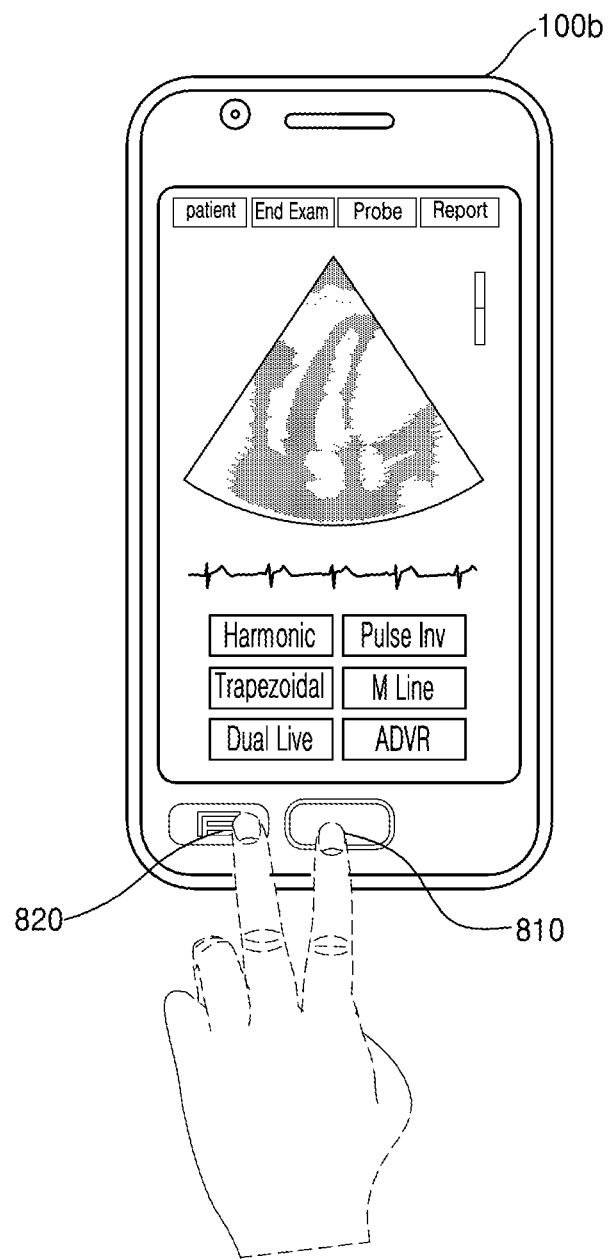
FIG. 8 is a diagram for describing a method of assigning a function to a combination of at least two fingerprints, according to an exemplary embodiment.

FIG. 8 is a diagram for describing a method of assigning a function to a combination of at least two fingerprints, according to an exemplary embodiment.

The apparatus 100 according to an exemplary embodiment may assign a function to a combination of at least two fingerprints of a user. For example, when a first function is assigned to an index finger fingerprint 810 of a left hand of the user and a second function is assigned to a middle finger fingerprint 820 of the left hand of the left hand, a third function, which is different from the first and second functions, may be assigned to a combination of the index finger fingerprint 810 and the middle finger fingerprint 820. The third function may be related to the first and second functions.

Referring to FIG. 8, the color Doppler image photography function may be assigned to the index finger fingerprint 810, and a freeze function may be assigned to the middle finger fingerprint 820. In this case, a function of freezing the color Doppler image may be assigned to the combination of the index finger fingerprint 810 and the middle finger fingerprint 820.

Accordingly, when the user touches a first key button by using the left hand index finger and touches a second key button by using the middle finger, the apparatus 100 may freeze the color Doppler image and display the frozen image on the display. However, exemplary embodiments are not limited thereto. Various functions may be assigned to the combination of at least two fingerprints according to user settings. Although FIG. 8 only illustrates an example in which the functions are assigned only to the combination of two fingerprints, the functions may be assigned to a combination of three fingerprints or a combination of four fingerprints.

Figure 9B:
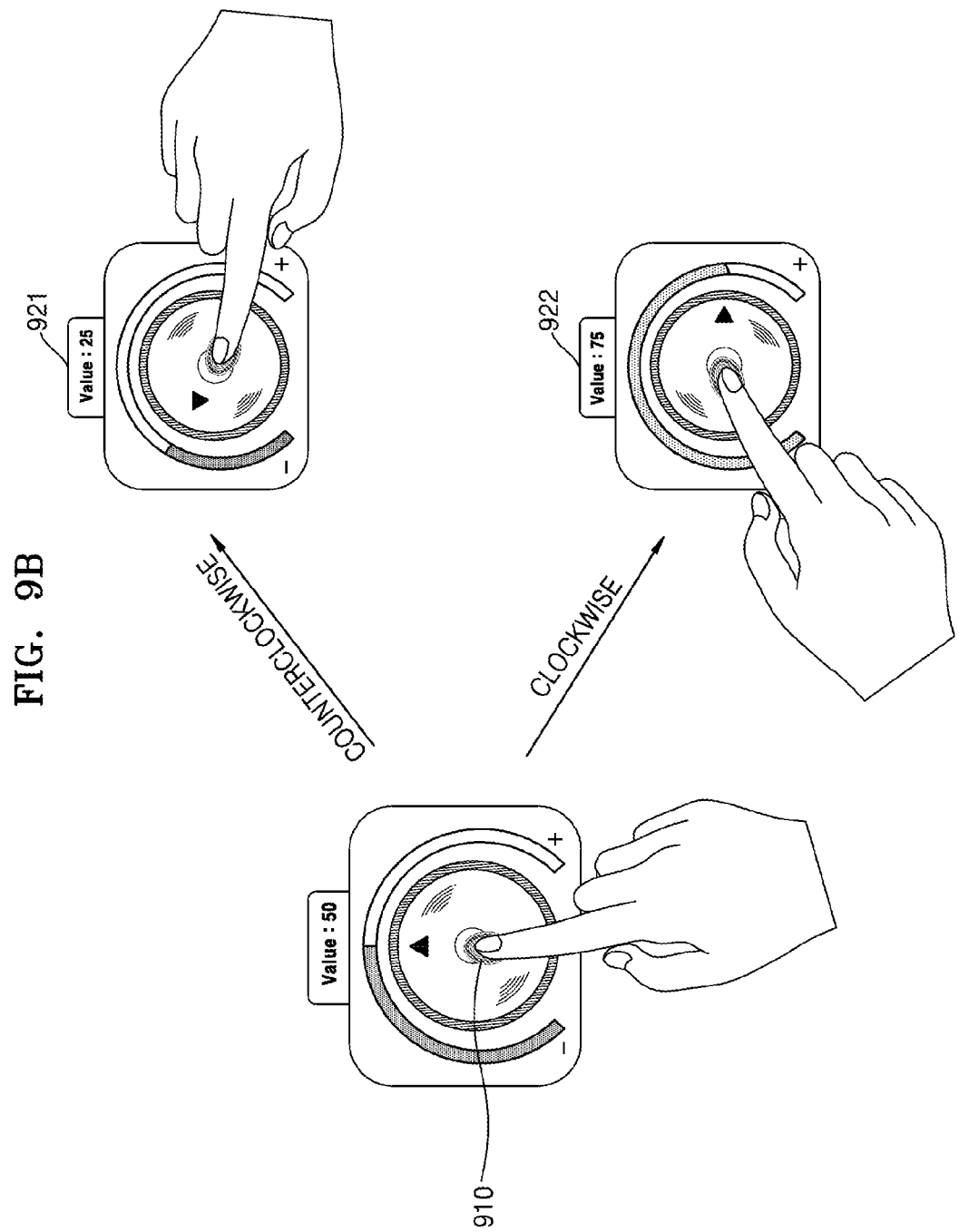

FIGS. 9A and 9B are diagrams for describing a method of adjusting values by using a fingerprint of a user, according to an exemplary embodiment.

Referring to FIG. 9A, when the user touches the user input unit 110 by using a first finger, the user input unit 110 may detect a fingerprint of the first finger by using the fingerprint sensor. Although FIG. 9A illustrates that the user input unit 110 is configured as a touch screen, the user input unit 110 is not limited thereto and may be configured as a dial, etc.

A function corresponding to the detected fingerprint may be a value adjustment function. For example, as shown in FIG. 9A, when a fingerprint 910 of a first finger is detected, a 2D image size adjustment menu may be selected. However, exemplary embodiments are not limited thereto. Any one of menus for adjusting values that are necessary for image processing (e.g., a clear vision index menu, a gray map menu, a frequency menu, or a TGC adjustment menu) may be selected.

Also, when the fingerprint 910 is detected and the 2D image size adjustment menu is selected, the user input unit 110 may display an indicator 905 indicating a current set value, and an increase or decrease of a value.

Referring to FIG. 9B, the apparatus 100 according to an exemplary embodiment may adjust a value according to a rotation direction and a rotation angle of the detected fingerprint 910. For example, the value may decrease when the fingerprint 910 rotates counterclockwise, and the value may increase when the fingerprint 910 rotates clockwise. The value may decrease or increase by a predetermined value when the fingerprint 910 rotates by a predetermined angle. For example, the value may decrease or increase by 5 when the fingerprint 910 rotates by 10°. Adjusted values 921 and 922 may be displayed on the touch screen or the display.

Whenever a detected fingerprint rotates by an angle, the apparatus 100 according to an exemplary embodiment may adjust an increased or decreased value according to a menu selected with respect to the detected fingerprint. For example, when the selected menu is a menu for adjusting a value within a large range (e.g., the 2D image size adjustment menu may have a size range of 10 to 100), the value may decrease or increase by 5 whenever a detected fingerprint rotates by 10°. Alternatively, when the selected menu is a menu for adjusting the value within a small range (e.g., a clear vision index adjustment menu may have an index range of 1 to 5), the value may decrease or increase by 1 whenever the detected fingerprint rotates by 10°.

According to an exemplary embodiment, a function set to a second finger fingerprint of the user may be the same as a function set to the first finger fingerprint of the user. For example, even when the second finger fingerprint is detected, the 2D image size adjustment menu may be selected. When the second finger fingerprint is detected and the 2d image size adjustment menu is selected, the apparatus 100 may adjust the value according to a rotation direction and a rotation angle of the second finger fingerprint. In the same manner as the first finger fingerprint, the value may decrease when the second finger fingerprint rotates counterclockwise, and the value may increase when the second finger fingerprint rotates clockwise. Alternatively, unlike the first finger fingerprint, the value may decrease when the second finger fingerprint rotates clockwise, and the value may increase when the second finger fingerprint rotates counterclockwise.

The apparatus 100 according to an exemplary embodiment may be set such that the value increases or decreases differently according to detected fingerprints even when the detected fingerprints are rotated by an identical angle and an identical menu is selected with respect to the detected fingerprints.

For example, when the second finger fingerprint is detected, unlike the case of the first finger fingerprint in which the value decreases or increases by 5 whenever the fingerprint rotates by 10°, the apparatus 100 may decrease or increase the value by 2 whenever the second finger fingerprint rotates by 10°.

Figure 10A:
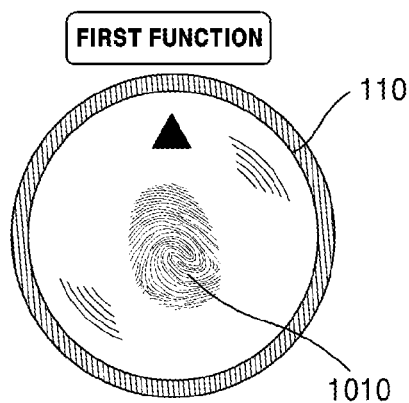
FIGS. 10A and 10B are diagrams of an example in which different functions are performed according to a direction of a fingerprint detected by an apparatus for processing medical images according to an exemplary embodiment.
Figure 10B:
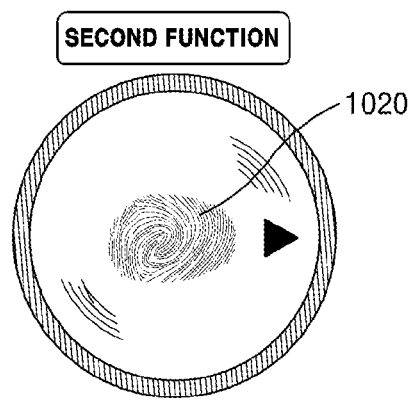

FIGS. 10A and 10B are diagrams of an example in which different functions are performed according to a direction of a fingerprint detected by an apparatus for processing medical images according to an exemplary embodiment.

The apparatus according to an exemplary embodiment may perform different functions according to the direction of the detected fingerprint.

Referring to FIG. 10A, when the user touches the user input 110 by using the first finger in a first direction, the user input unit 110 may detect a first finger fingerprint 1010 in the first direction by using the fingerprint sensor. The apparatus 100 may perform a first function that corresponds to the detected first finger fingerprint 1010 in the first direction. The first function may be an S-Detect function that is for detecting lesions and analyzing characteristics of the detection lesions.

Accordingly, when the first finger fingerprint in the first direction is detected, the apparatus 100 may display an S-Detect execution screen on the display.

Referring to FIG. 10B, when the user touches the user input 110 by using the first finger in a second direction, the user input unit 110 may detect a first finger fingerprint 1020 in the second direction by using the fingerprint sensor. The apparatus 100 may perform a second function that corresponds to the detected first finger fingerprint 1020 in the second direction. The second function may be an elastoscan for breast (E-Breast) function. The E-Breast function is used to detect a tumor and diagnosing the tumor, and a color bar is provided. An average strain value in a frame of an ultrasound image may be set to a median of the color bar. Based on the median, an area with a large strain value may be detected as a soft area, and an area with a small strain value may be detected as a hard area. The median area may be shown in green, the soft area may be shown in blue, and the hard area may be shown in red. However, exemplary embodiments are not limited thereto.

Accordingly, when the first finger fingerprint 1020 in the second direction is detected, the apparatus 100 may display, on the display, an elastoscan image according to the above-described color bar.

Figure 11:
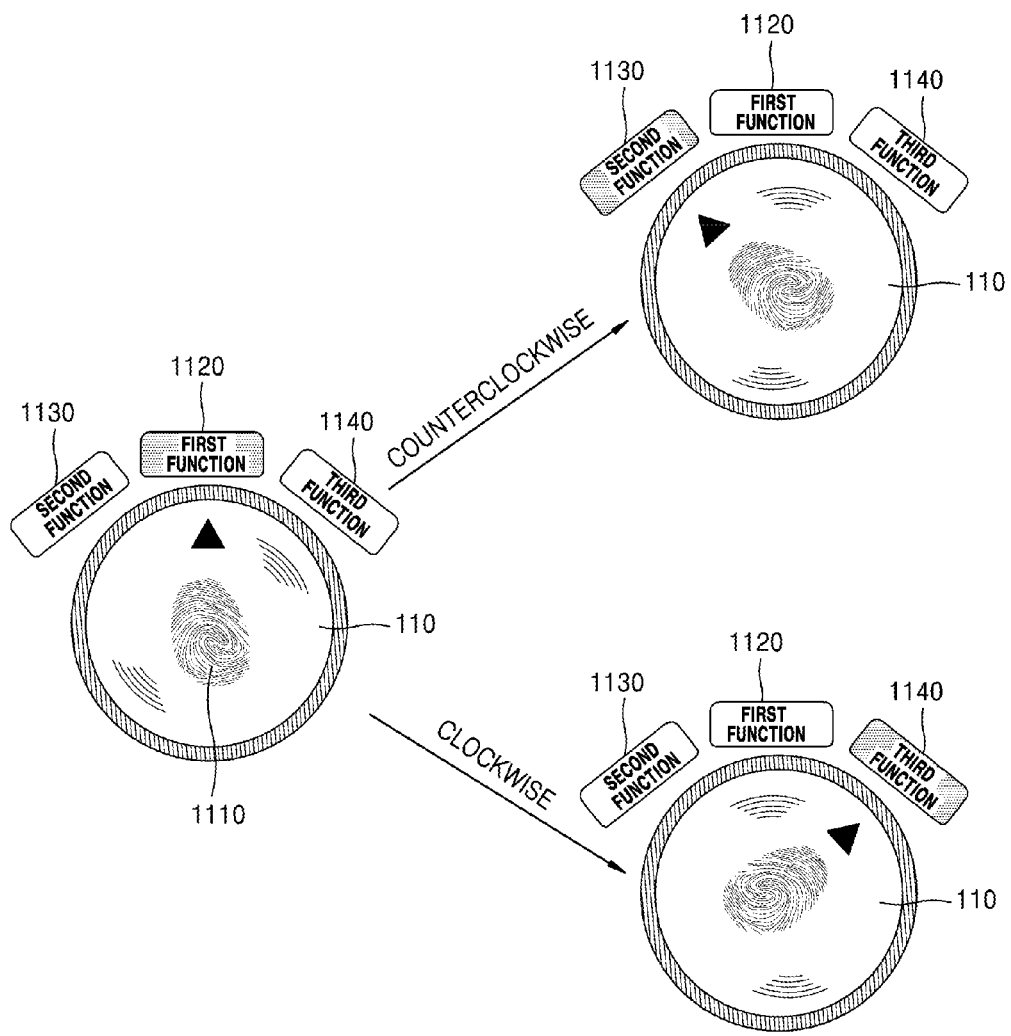
FIG. 11 is a diagram of an example in which different functions are performed as a fingerprint detected by an apparatus for processing medical images rotates, according to an exemplary embodiment.

FIG. 11 is a diagram of an example in which different functions are performed as a fingerprint detected by an apparatus for processing medical images rotates, according to an exemplary embodiment.

Referring to FIG. 11, when the user touches the user input unit 110 by using a first finger, the user input unit 110 may detect a fingerprint 1110 of the first finger by using the fingerprint sensor. A first function corresponding to the detected fingerprint 1110 may be the S-Detect function. Then, the apparatus 100 may display, on the touch screen or the display, guide information 1120 indicating that the first function corresponding to the fingerprint 1110 is the S-Detect function. Also, when the user touches the user input unit 110 by using the first finger and rotates the first finger clockwise or counterclockwise, the apparatus 100 may further display guide information 1130 and 1140 indicating that another function may be performed.

Referring to FIG. 11, when the user rotates the first finger clockwise by a first angle while touching the user input unit 110 with the first finger, the apparatus 100 may perform a second function. The second function may include, but is not limited to, the PW-Mode function for capturing a power Doppler image.

Alternatively, when the user rotates the first finger clockwise by a second angle while touching the user input unit 110 with the first finger, the apparatus 100 may perform a third function. The third function may include, but is not limited to, the E-Breast function.

Figure 12:
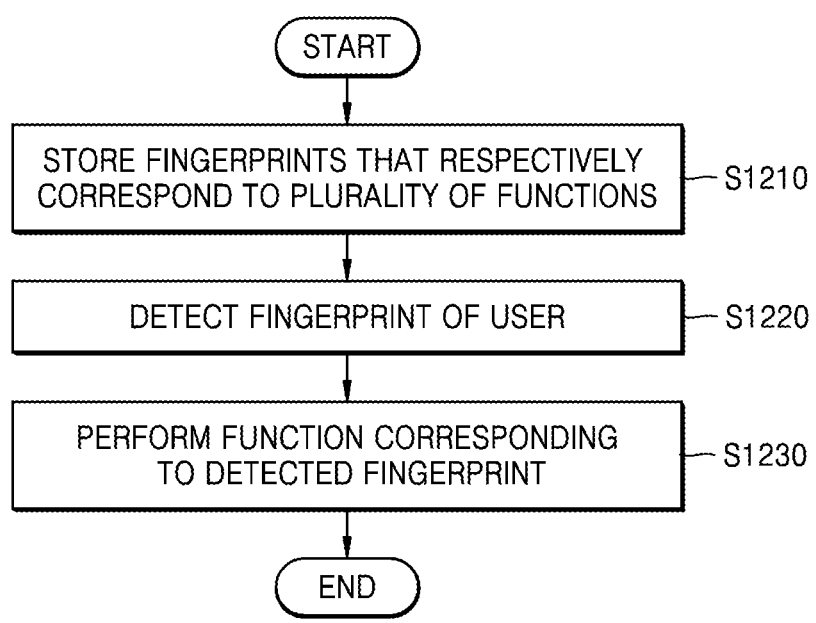
FIG. 12 is a flowchart of a method of operating an apparatus for processing medical images, according to an exemplary embodiment.

FIG. 12 is a flowchart of a method of operating an apparatus for processing medical images, according to an exemplary embodiment.

Referring to FIG. 12, the apparatus 100 according to an exemplary embodiment may be store fingerprints that respectively correspond to functions (S1210).

The apparatus 100 may store the fingerprints that respectively correspond to the functions that are performed to process the medical images. The functions may include, but is not limited to, the Doppler image photography function (the color Doppler image photography function or the power Doppler image photography function), the pulse wave measurement function, the freeze function, the TGC adjustment function, the focus selection function, the parameter measurement function, the storage function, the S-Detect function, and the E-Breast function.

For example, the apparatus 100 may set a thumb fingerprint of a first user as a fingerprint corresponding to a first function from among the functions, and set an index finger fingerprint of the first user as a fingerprint corresponding to a second function from among the functions. Also, a combination of the index finger fingerprint and a middle finger fingerprint of the first user may be set as a fingerprint corresponding to a third function.

The apparatus 100 may detect a fingerprint of the user (S1220).

For example, the apparatus 100 may include a fingerprint sensor and detect the fingerprint of the user by using the fingerprint sensor. The fingerprint sensor may be included in a touch screen, a touch panel, a key button, a knob button, a trackball, a dial, etc.

The apparatus 100 may perform a function that corresponds to the detected fingerprint (S1230).

For example, the apparatus 100 may perform a first function that corresponds to a first fingerprint when the first fingerprint is detected, and perform a second function that corresponds to a second fingerprint when the second fingerprint is detected. Also, the apparatus 100 may perform a third function when the first and second fingerprints are simultaneously detected.

Also, when the function corresponding to the detected fingerprint is a function of adjusting a value, the apparatus 100 may adjust the value according to a rotation direction and a rotation angle of the detected fingerprint. For example, when the detected fingerprint is the first fingerprint, the apparatus 100 may increase or decrease the value by a first value when the first fingerprint rotates by a predetermined angle. When the detected fingerprint is the second fingerprint, the apparatus 100 may increase or decrease the value when the second fingerprint rotates by a predetermined angle.

The apparatus 100 may perform a function different from the function corresponding to the detected fingerprint, based on the rotation direction and the rotation angle of the detected fingerprint.

The ultrasound diagnosis apparatus and the method of operating the same according to the exemplary embodiments can also be embodied as computer-readable codes on a non-transitory computer-readable recording medium. The non-transitory computer-readable recording medium is any data storage device that can store data which can thereafter be read by a computer system. Examples of the non-transitory computer-readable recording medium include read-only memory (ROM), random-access memory (RAM), CD-ROMs, magnetic tapes, floppy disks, optical data storage devices, etc. The non-transitory computer-readable recording medium can also be distributed over network coupled computer systems so that the computer-readable code is stored and executed in a distributive manner.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for processing medical images, the apparatus comprising:
    a storage configured to store fingerprints that respectively correspond to a plurality of functions;
    a user input unit configured to detect a fingerprint of a user and receive a touch and drag input based on a point where the fingerprint has been detected; and
    a controller configured to, in response to detecting the fingerprint of the user and receiving the touch and drag input, control a display to display an object corresponding to the touch and drag input, and perform a function corresponding to the detected fingerprint based on the object.

2. The apparatus of claim 1, wherein the display displays guide information that is related to the function corresponding to the detected fingerprint.

3. The apparatus of claim 1, wherein the user input unit comprises a touch screen, and
    the touch screen displays, at the point where the fingerprint of the user is detected, guide information related to the function corresponding to the detected fingerprint.

4. The apparatus of claim 1, wherein the functions comprise a time gain compensation (TGC) adjustment function and the object comprises a TGC curve, the controller sets a TGC value based on the TGC curve.

5. The apparatus of claim 1, wherein when a first fingerprint of the user is detected, the controller performs a first function corresponding to the first fingerprint from among the functions based on the object, and when a second fingerprint of the user is detected, the controller performs a second function corresponding to the second fingerprint from among the functions based on the object.

6. The apparatus of claim 5, wherein when the first and second fingerprints are detected, the controller performs a third function from among the functions based on the object.

7. A method of operating an apparatus for processing medical images, the method comprising:
    storing fingerprints that respectively correspond to a plurality of functions;
    detecting a fingerprint of a user;
    receiving a touch and drag input based on a point where the fingerprint has been detected;
    in response to detecting the fingerprint of the user and receiving the touch and drag input, displaying an object corresponding to the touch and drag input; and
    performing the function corresponding to the detected fingerprint based on the object.

8. The method of claim 7, further comprising displaying guide information that is related to the function corresponding to the detected fingerprint.

9. The method of claim 8, wherein the displaying of the guide information comprises displaying, at the point where the fingerprint of the user is detected, guide information related to the function corresponding to the detected fingerprint.

10. The method of claim 7, wherein the functions comprise a time gain compensation (TGC) adjustment function and the object comprises a TGC curve, wherein the performing the function corresponding to the detected fingerprint comprises setting a TGC value based on the TGC curve.

11. The method of claim 7, wherein the performing the function corresponding to the detected fingerprint comprises, when a first fingerprint of the user is detected, performing a first function corresponding to the first fingerprint from among the functions based on the object, and when a second fingerprint of the user is detected, performing a second function corresponding to the second fingerprint from among the functions based on the object.

12. The method of claim 11, wherein the performing function corresponding to the detected fingerprint further comprises, when the first and second fingerprints are detected, performing a third function from among the functions based on the object.

13. A non-transitory computer-readable recording medium having recorded thereon a program, which, when executed by a computer, performs the method of claim 7.

14. The apparatus of claim 1, wherein the controller performs a first function, in response to detecting the fingerprint in a first direction, and performs a second function different from the first function, in response to detecting the fingerprint in a second direction different from the first direction.

* * * * *